United States Patent [19]

Wang et al.

[11] Patent Number: 4,838,278
[45] Date of Patent: Jun. 13, 1989

[54] PACED QRS COMPLEX CLASSIFIER

[75] Inventors: Jyh-Yun Wang, Newton; Mousa N. Shaya, Waltham, both of Mass.

[73] Assignee: Hewlett-Packard Company, Palo Alto, Calif.

[21] Appl. No.: 19,270

[22] Filed: Feb. 26, 1987

[51] Int. Cl.⁴ ............................................... A61B 5/04
[52] U.S. Cl. .................................................... 128/697
[58] Field of Search ............... 128/696, 697, 703, 704, 128/708

[56] References Cited

U.S. PATENT DOCUMENTS

| | | | |
|---|---|---|---|
| 3,742,938 | 7/1973 | Stern | 128/419 PT |
| 3,782,367 | 1/1974 | Hochberg et al. | 128/419 PT |
| 3,946,744 | 3/1976 | Auerbach | 128/419 PT |
| 4,088,139 | 5/1978 | Auerbach | 128/419 PT |
| 4,144,892 | 3/1979 | Auerbach | 128/419 PT |
| 4,164,227 | 8/1979 | Auerbach | 128/419 PT |
| 4,583,553 | 4/1986 | Shah et al. | 128/708 |

Primary Examiner—Francis Jaworski
Assistant Examiner—George Manuel
Attorney, Agent, or Firm—Donald N. Timbie

[57] ABSTRACT

Apparatus for classifying QRS complexes as dual chamber paced, atrially paced or ventricularly paced by assigning complexes to groups in accordance with shape, deriving the intervals between pace pulses and their respective QRS complexes, determining if the intervals for a given number of recent complexes from the group to which the current QRS complex is assigned are clustered, and classifying the current QRS complex by the correlation between the intervals of its pace pulses and the intervals of said clusters.

7 Claims, 9 Drawing Sheets

| NO. | WAVE SHAPE | NO. OF BEATS OF THIS SHAPE | CLASSIFICATION OF THIS SHAPE | PACE PULSES TO BEAT INTERVALS | ... |
|---|---|---|---|---|---|
| 1 | ⌇ | 7 | • | • | |
| 2 | ⌇ | 3 | • | • | |
| 3 | ⌇ | 4 | • | • | |
| ...... | ...... | ...... | ...... | ...... | |

FIG 4

PACED QRS COMPLEX CLASSIFIER

BACKGROUND OF THE INVENTION

The analysis of ECG waveforms using computerized arrhythmia monitoring systems consists of several steps. First each QRS complex must be detected and classified into a normal and abnormal categories. Subsequent analysis on the timing and pattern of these beats will yield alarms with several priorities to be annunciated to the user for treatment of the patient.

The patient population can be broken into two groups, patients with pacemakers and patients without pacemakers. Non-paced patients generate abnormal QRS complexes i.e. beats that are quite different in shape from their normal counterparts. However, paced patients generate paced beats initiated by the pacemaker that are treated as normal beats. These paced beats are substantially similar in wave shape to their abnormal counter-parts. Thus computerized arrhythmia monitoring systems designed for non-paced patients generate a high level of false alarms.

Some systems employ a simplistic approach to reduce false alarms by classifying any beat that is preceded by a pace pulse, as a paced beat. However this does not significantly reduce false alarms. Pace pulses can appear to be generated by noise in the ECG signals or be ineffective pace pulses that have not initiated any beat as to indicate an abnormal pacemaker operation. Such ineffectual pace pulses and false pace pulse indications may preceed abnormal beats which are misclassified as paced beats.

A group of similarly shaped QRS complexes, that are pacemaker initated, have pace pulses at a constant distance prior to the beats in this group.

The interval between the QRS complex and the preceding pace pulse is larger for atrially paced beats than ventricularly paced beats because of the delay in normal conduction of the pacing stimulus from the atrium to the ventricles. This relationship between atrial and ventricular pace pulse intervals to the QRS complex remains the same for dually paced beats.

BRIEF SUMMARY OF THE INVENTION

If the times of occurence of pace pulses and QRS complexes could be determined without error, and if the intervals between them remained constant, it would not be difficult to classify the complexes as being dual chamber paced, atrially paced, ventricularly paced, normal or other and therefore not paced, but means for detecting the time of occurrence of a pace pulse can give false positive or false negative indications because of the presence of noise, artifacts and body movement as well as physiological factors that can change the shape of a QRS complex so as to make it difficult to say precisely when it occurs. Furthermore, the pacemakers themselves may provide erroneous signals or may not produce the desired signals so that classification on a beat by beat basis would be in error. In fact one of the reasons for classifying the QRS complexes in an ECG wave is to monitor the operation of the pacer.

In accordance with this invention, the time at which a QRS complex is received is provided and the complex is stored with a group of complexes having the same shape in accordance with existing techniques. A pace pulse detector provides the times of occurrence of pace pulses, and means are provided for determining the interval between each pace pulse and the next QRS complex. These intervals are stored with that complex. Means are provided for determinig whether the intervals for the last complexes of the group to which the current complex has been assigned are clustered about differente values, and other means derive the average value of the intervals occurring in each cluster. A small average value may be designated as ds, and a large average value may be designated as d1. These values are stored in a template buffer. If no clusters are found, there are no average values and nothing to be stored in the template buffer.

The occurrence of a value ds is an indication that the QRS's in the group to which the current complex has been assigned are ventricularly paced; the occurence of a value d1 is an indication that they are atrially paced; the occurence of ds and d1 is and indication that they are dual chamber paced, and the absence of both ds and d1 is an indication that they are derived from normal beats in which the heart is not reacting to a pace pulse even though it may be present. These indications are stored in the template buffer.

Whereas the probable classification of the current QRS complex can be derived from these indications, a more reliable classification is obtained from certain known facts and the correlation between these indications and the intervals for pace pulses associated with the current QRS complex. By way of example, if two clusters at ds and d1 are found for the group of QRS complexes to which the current complex has been assigned and the complex has a pace pulse at an interval that is very close to d1, it will be classified as dual-chamber paced. Other correlations will be described in the detailed description of the invention.

BRIEF DESCRIPTION OF THE DRAWINGS

FIG. 4 illustrates what is stored in a template storage buffer of FIG. 3.

DETAILED DESCRIPTION OF THE INVENTION

Figure 1:
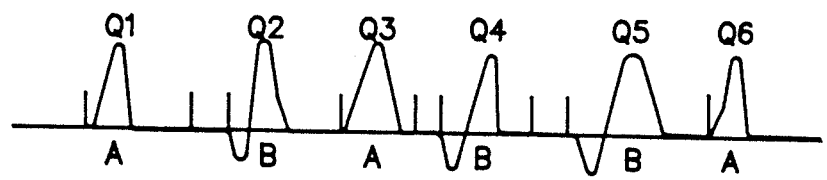
FIG. 1 illustrates a series of QRS complexes of two different groups or shapes A and B and their accompanying pace pulses.

In FIG. 1 six QRS complexes Q1 through Q6 are shown. The complexes Q1, Q3 and Q6 form a group having shapes that while not identical are sufficiently similar to be classified as a shape A, and the complexes Q2, Q4 and Q5 form a different group having shapes that while not identical are sufficiently similar to be classified as a shape B.

Figure 1A:
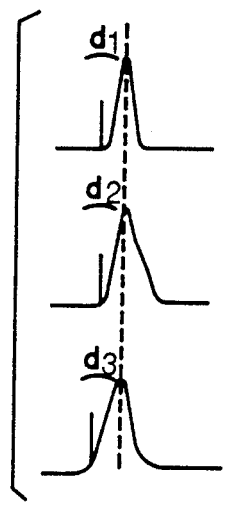
FIG. 1A shows the complexes of the group having the shape A in vertical alignment so that the distances of the single pace pulses from their respective QRS complexes may be more readily compared, FIG. 1A' illustrates the clustering of the distances for the group A.

Single pace pulses are shown ahead of each of the complexes having the shape A. These complexes are vertically aligned in FIG. 1A so that it can be seen that the intervals between the single pace pulses and their respective QRS complexes are very close to the same values. FIG. 1A' is a histogram showing at CA the clustering or distribution of these intervals.

Figure 1B:
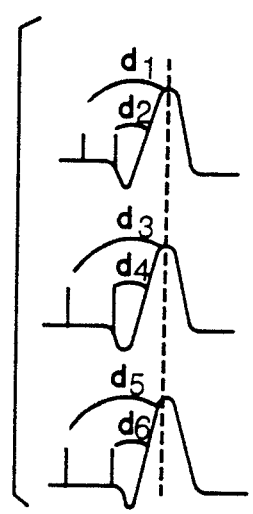
FIG. 1B shows the complexes of the group B in vertical alignment so that the distances of the dual pace pulses from their respective QRS complexes may be more readily compared, FIG. 1B' shows the clustering of the distances for the group of complexes shown in FIG. 1B.
Figure 1A:
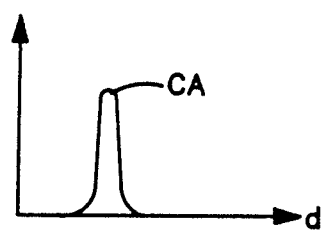
Figure 1B:
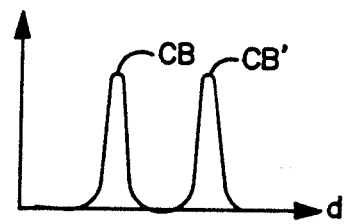

A pair of pace pulses are shown ahead of each of the complexes having the shape B. These complexes are vertically aligned in FIG. 1B so that it can be seen that the intervals between corresponding ones of each pair of pace pulses and their respective QRS complex are very close to the same value. FIG. 1B' is a histogram showing at CB the clustering or distribution of short intervals for pace pulses closer to their respective complexes and at CB' the clustering or distribution of long intervals for the pace pulses farther from their respective complexes.

Figure 2:
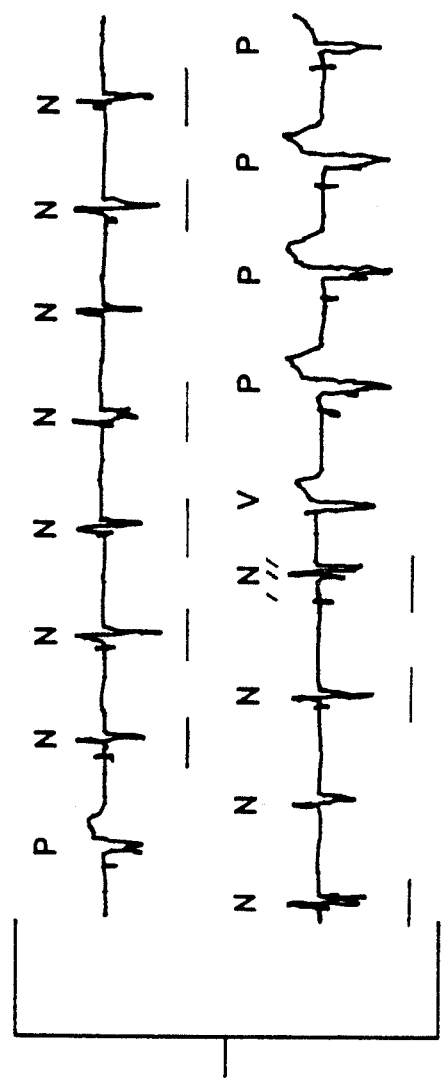
FIG. 2 shows an ECG signal and the classifications of the QRS complexes that would be made by monitoring apparatus incorporating this invention.

FIG. 2 shows a series of QRS complexes having an N over them when they would be classified as normal by the algorithm of this invention because the distance between the pace pulses and their respective QRS complexes varies. This is a proper classification, but those that are underlined would be erroneously classified as paced by an algorithm that asserts such a classification merely because the pace pulse accompanies the QRS complex.

Figure 3:
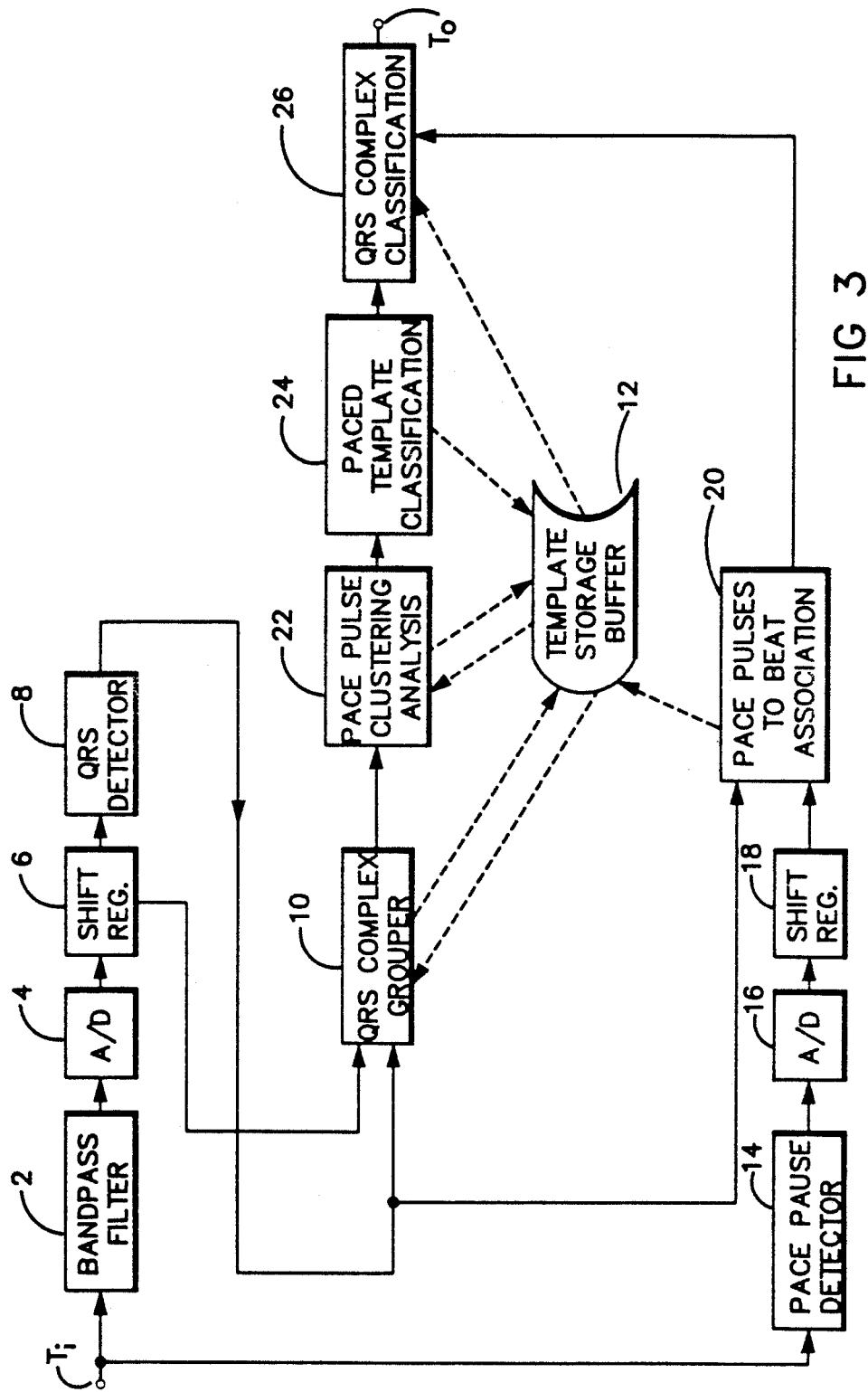
FIG. 3 is a block diagram of a monitoring apparatus incorporating this invention.

FIG. 3 is a block diagram of a QRS classification system that operates in accordance with this invention. ECG signals are applied to an input terminal Ti. After passing through a band pass filter 2 that may have a lower cut-off frequency of 0.5 Hz for eliminating base line wander, the ECG signals are applied to and A/D converter 4. If its sampling rate is 500 Hz, the provision of an upper cut-off frequency of 125 Hz for the band pass filter 2 has been found satisfactory.

The samples emerging from the A/D converter 4 are applied via a shift register 6 to a QRS detector 8 that, as is well known by those skilled in the art, supplies a signal at its output indicating the time of the peak of the R wave of a QRS complex.

A QRS complex grouper 10 that is coupled to the shift register 6 and the output of the QRS dectector 8 updates beat shapes it previously stored in a template storage buffer 12, representing different shapes of QRS complexes. The function is well understood by those skilled in the art so as to require no futher description. The contents of the template buffer 12 illustrated in FIG. 4 contain updated templates of the various shapes of QRS complexes encountered, the number of them that have occured, and the classification of each shape.

A pace pluse detector 14 is connected between the input terminal Ti and an A/D converter 16, and its output is applied to a shift register 18.

A means 20 is provided for establishing the differences in time between the current QRS complex detected by the QRS detector 8 and the pace pulses detected by the detector 14. The pace pulses are those that occured within a given interval between the current QRS complex and the previous one. The output of the QRS detector 8 and the shift register 18 are coupled to the means 20. The difference in time is stored in the template storage buffer 12 in association with its QRS complex.

A means 22 is provided for deriving the clustering information for each of the last QRS complexes of the shape group to which the current QRS belongs. In particular, it provides a signal OPs=1 if at last six of the last 8 of the QRS complexes of the shape group including the current QRS have pace pulse intervals within a narrow cluster centered at a short time prior to their respective QRS complexes, in which event the average ds of all these intervals is derived. If the condition does not exist set OPs=0.

Similarly, the means 22 provides a signal OPl=1 if at least six of the last eight of the QRS complexes have pace pulse intervals within a narrow cluster centered at a long time prior to their respective QRS complexes, in which event the average dl of all these times is derived. If the condition does not exist, set OPl=0.

For each shape group, a means 24 derives a paced template classification determined from the signals OPs, OPl, ds and dl whether the classification for the group should be dual-chamber paced, atrial chamber paced, ventricular chamber paced or not paced and stores it in the template buffer 12.

Finally, a means 26 is provided for classifying the current QRS complex. If the last eight QRS complexes for a given shape including the current one causes the paced template classification means 24 to indicate a non paced condition, i.e. if OPs=0 and OPl=0, the classification must be made by some other means.

FLOW CHARTS

Pace Pulse to Beat Association Means 20

Figure 5:
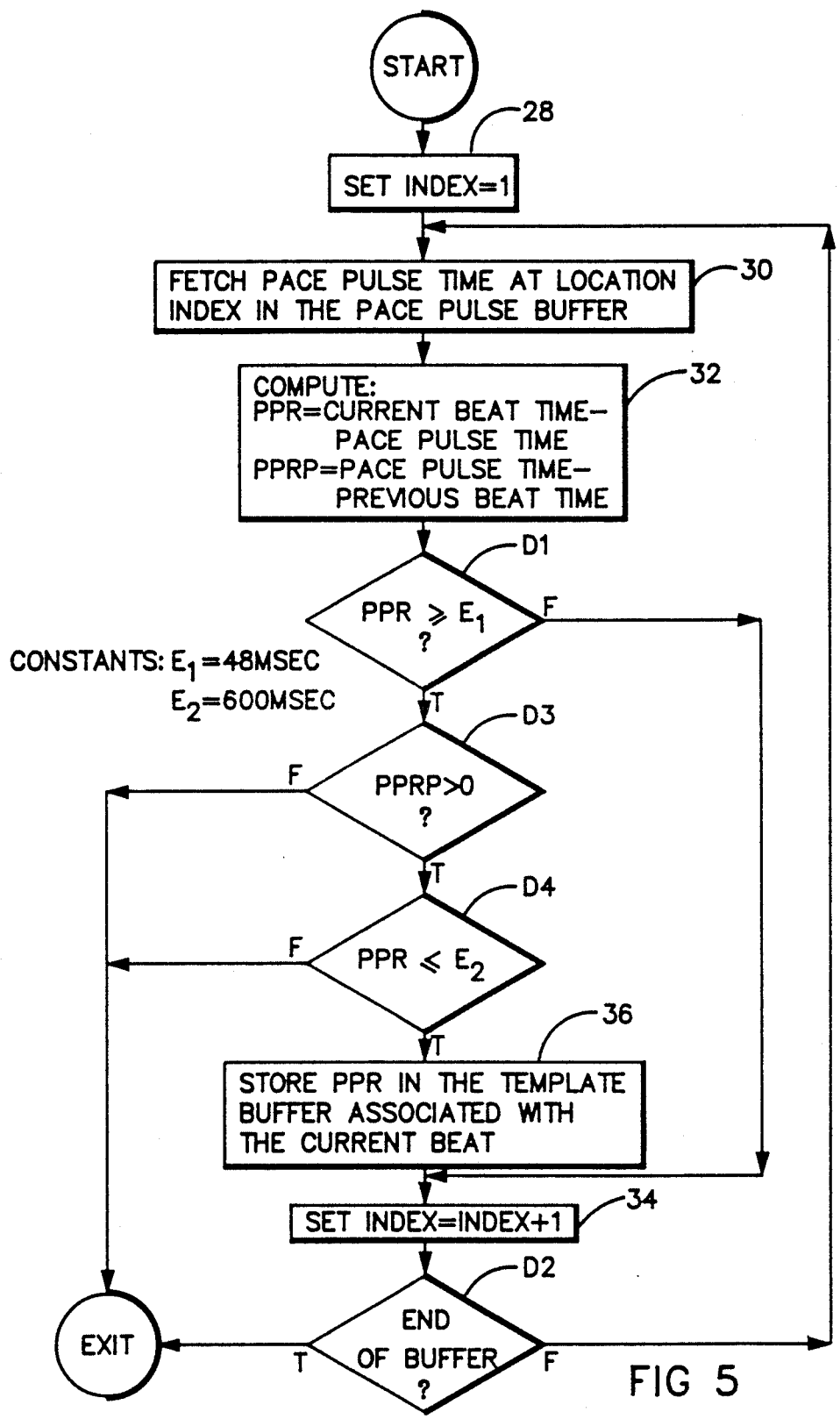
FIG. 5 is a flow chart for identifying Pace Pulses associated with QRS complexes.

The purpose of this procedure, FIG. 5, is to store in the template storage buffer 12 the intervals between each pace pulse and the peak of the succeeding R wave that falls within a time window. In this example the time window extends from 48 to 600 msec before the the R wave peak. Every time a pace pulse is detected its time of occurrence is stored in the shift register 18, and every time a QRS is detected its time of occurrence is known. The procedure starts with block 28 that sets the index or pointer for the pace pulse shift register 18 at the end where the time of the latest pace pulse is stored. A block 32 then computes the difference PPR between the time of the current QRS and the time at time index in the shift register 18. It also computes the difference PPRP between the pace pulse time at time index and the time of the previous QRS complex.

A decision block D1 then checks to see if PPR≧E1 where E1 is the shortest interval between a pace pulse and a QRS complex that will be used. In this embodiment E1 is 48 msec. If PPR is less than E1, D1 gives a flase indication and the procedure goes to a block 34 which increases the time index by one. A decision block D2 then indicates whether the procedure has reached the end of the shift register 18. If not, the procedure is repeated until the output of D1 is true.

When this occurs, D3 checks to see if PPRP>0, then a decision block D4 checks to see if PPR≦E2, which in this embodiment is 600 msec. If the time of a pace pulse fetched from the shift register 18 is between 48 and 600 ms earlier than the time of the current QRS a block 36 stores the value of PPR in the template buffer 12 with the current QRS complex. The block 34 then increases the time index and the process is repeated unitl D2, D3 or D4 indicates a false condition.

Pace Pulse Clustering Analyses Means 22

Figure 6A:
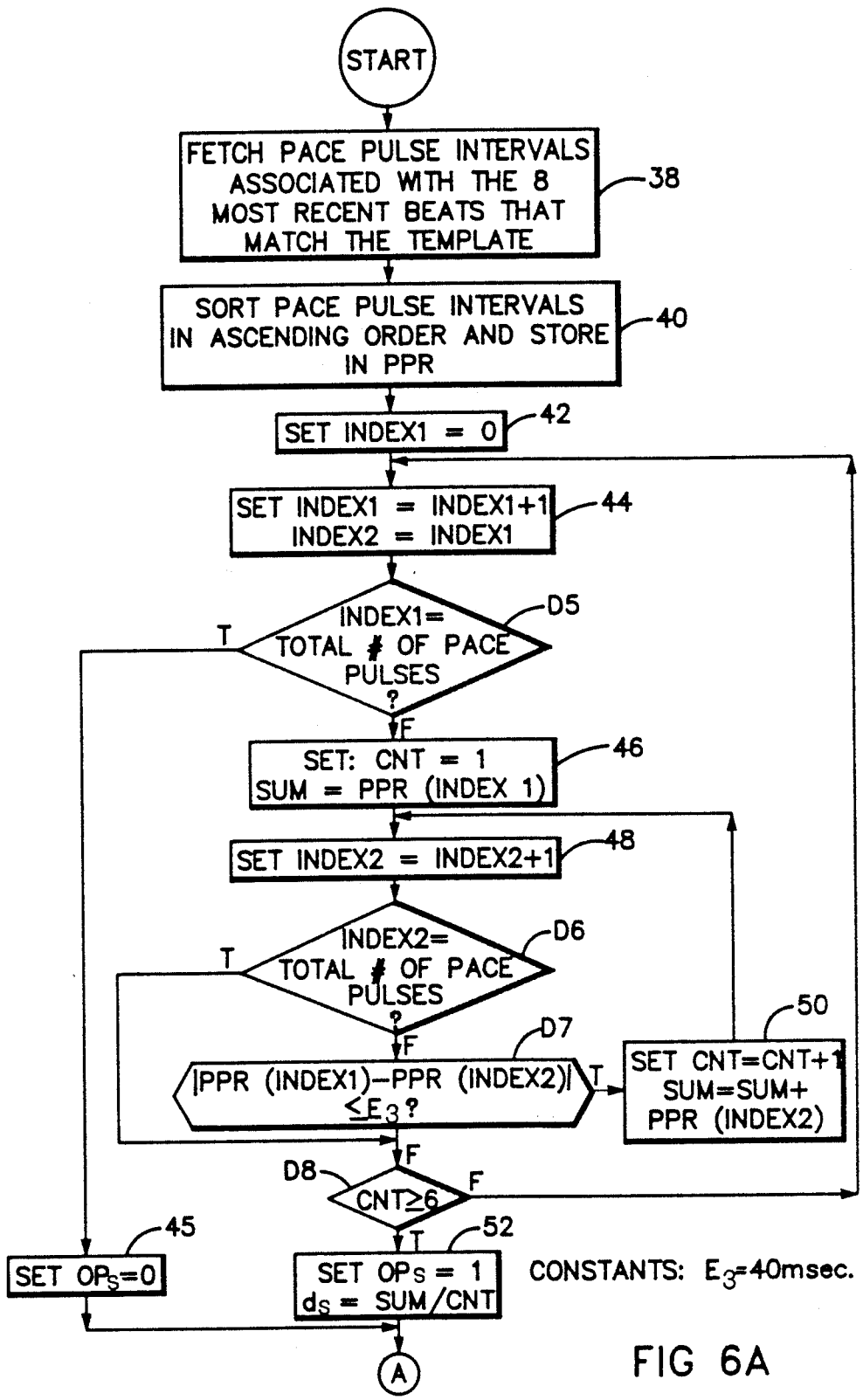
FIG. 6A is a flow chart for determining certain values related to pace pulse clustering.
Figure 6B:
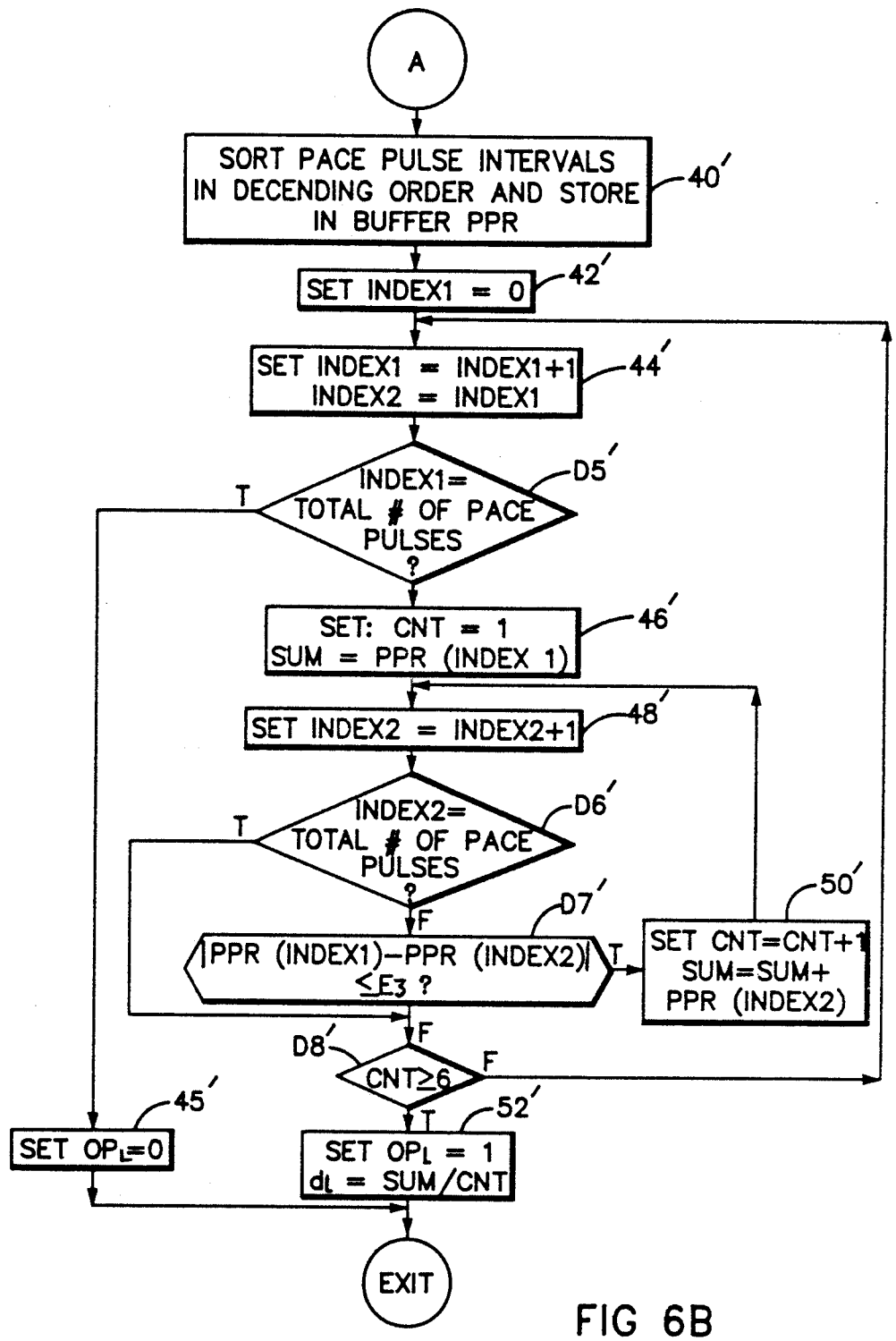
FIG. 6B is a flow chart for determining other values related to pace pulse clustering.

The purpose of this means, FIGS. 6A and 6B, is to examine the PPR values that have been stored in the template storage buffer 12 by the block 36 of FIG. 5 for the last n QRS complexes having the same shape classification as the current complex to see if there are m PPR intervals differing by less than E3 seconds from each other. In one embodiment of this invention $n=8$, $m=6$ and $E3=40$ msec. If so, a cluster exists. A cluster of short intervals can be found by examining the PPR intervals in ascending order of magnitude as in FIG. 6A and a cluster of long intervals can be found by examining the PPR intervals in descending order of magnitude as in FIG. 6B. If a cluster of smaller intervals is found, a signal $OPs=1$ is produced and the average ds of these intervals is provided. If no such cluster in found, a signal $OPs=0$ is produced. If a cluster of larger intervals is found, a signal $OP1=1$ is produced and the average d1 of these intervals is provided. If no such cluster is found, a signal $OP1=0$ is produced.

The procedure of FIG. 6A is as follows. A block 38 fetches the pace pulse PPR intervals stored in the buffer 12 for the last 8 QRS complexes having the same shape classification as the current QRS complex, and a block 40 arrange these intervals in ascending order in the buffer 12, and provides their total number. A block 42 initializes the procedure by setting an $index1=0$, and a block 44 increments index1 by one and sets an index2 to the same value.

Decision block D5 checks to see if index1 exceeds the total number of PPR intervals. If it does, a block 45 sets $OPs=0$, but if not, a block 46 sets a counter equal to 1 and a summer equal to the first PPR interval in the buffer, which is at index1. A block 48 increments index2 by one so that it is at the next PPR interval beyond index1 and D6 checks to see if inde2 exceeds the number of stored PPR intervals. If not, D7 checks to see if the difference between the PPR interval at index1 and the PPR interval at index2 is less than a given value E3, which in this embodiment is 40 msec. If so, a block 50 increments the counter by one and increments the summer by the value of the PPR interval at index2. This process can continue until D6 indicates that there are no more PPR intervals in the buffer, or if the difference between the PPR values at index2 and index1 is greater than E3. Decision block D8 checks to see if the counter is greater than or equal to 6. If not, the procedure reverts to block 44 that increments index1 by one and sets index2 equal to index1.

Whenever D8 indicates a count of 6 or more, a block 52 set $OPs=1$ and derives ds by dividing the sum in the summer by the count in the counter.

In FIG. 6B components corresponding to FIG. 6A have the same designations primed. The only difference is that the block 40' arranges the PPR values in descending order. It, of course, provides the signals $OP1=0$, $OP1=1$ and d1.

PLACED TEMPLATE CLASSIFICATION 24

Figure 7:
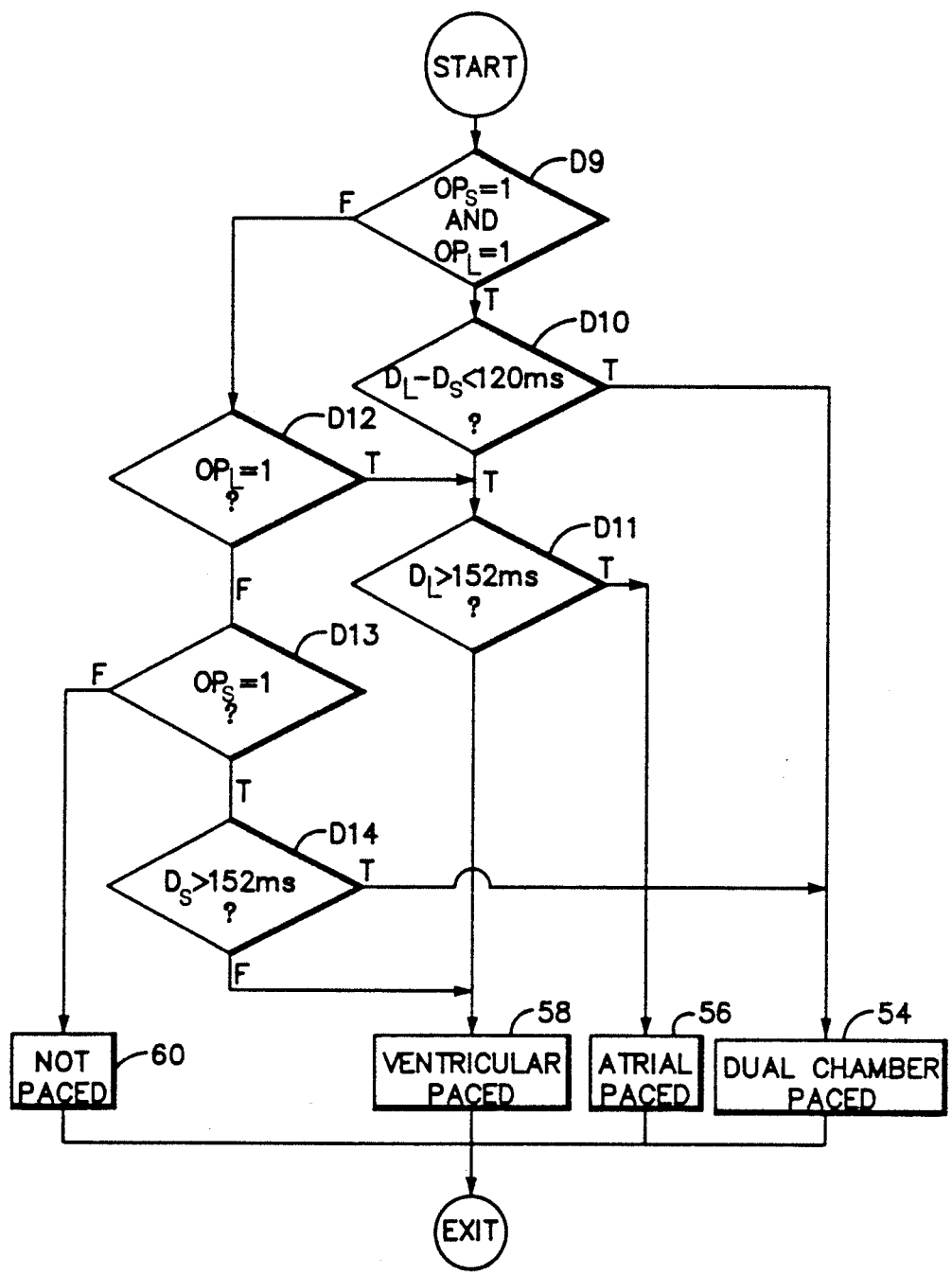
FIG. 7 is a flow chart for utilizing the values provided in accordance with the flow charts of FIGS. 6A and 6B for the purpose of updating a template classification for each group.

The purpose of this procedure, FIG. 7, is to utilize the information about clusters and average values thereof provided by the procedures of FIGS. 6A and 6B to store information in the template storage buffer 12 as to whether QRS complexes having the shape of the current QRS complex are placed or not and if so, whether they are dually paced, atrially paced or ventricularly paced.

If D9 indicates that $OPs=1$ and that $OP1=1$, it means that there are two clusters so as to indicate the probability of dual chamber pacing, but a further check is made by D10 to see if the difference d1−ds between the average values of the clusters is less than a given amount herein indicated as being 120 ms. If the difference is not less than this amount, block 54 provides an indication to the template storage buffer 12 that the shape of the QRS complex just examined should be classified as dual chamber paced.

On the other hand if D10 indicates that the time d1−ds is less than a given amount, the clusters are too close together for dual chamber pacing. D11 determines whether atrial pacing or ventricular pacing is involved by checking to see if d1 is greater than a given time, herein indicated as being 152 msec. If it is, a block 56 stores in the template buffer 12 information, that atrial pacing is invloved, but if it is not, a block 58 stores information in the buffer indicating that ventricular pacing is involved.

Should D9 give a flase indication meaning that both clusters do not exist at the same time, D12 checks to see if a cluster of long intervals exists. If $OP1=1$, it does and the procedure goes to D11 again. But if $OP1=0$, D13 checks to see if a cluster of short intervals exists by checking OPs. If $OPs=1$ a cluster of short intervals does exist and D14 checks ds. If $ds>152$ msec, the single cluster indicates atrial pacing so that the procedure goes to the block 56, but if ds is less than or equal to 152 msec, a block 58 indicates that ventricular pacing is involved.

If D13 indicates that $OPs=0$, no clusters exist so that pacing is not involved, and a block 60 stores this fact in the template buffer 12.

QRS CLASSIFICATION 26

Figure 8:
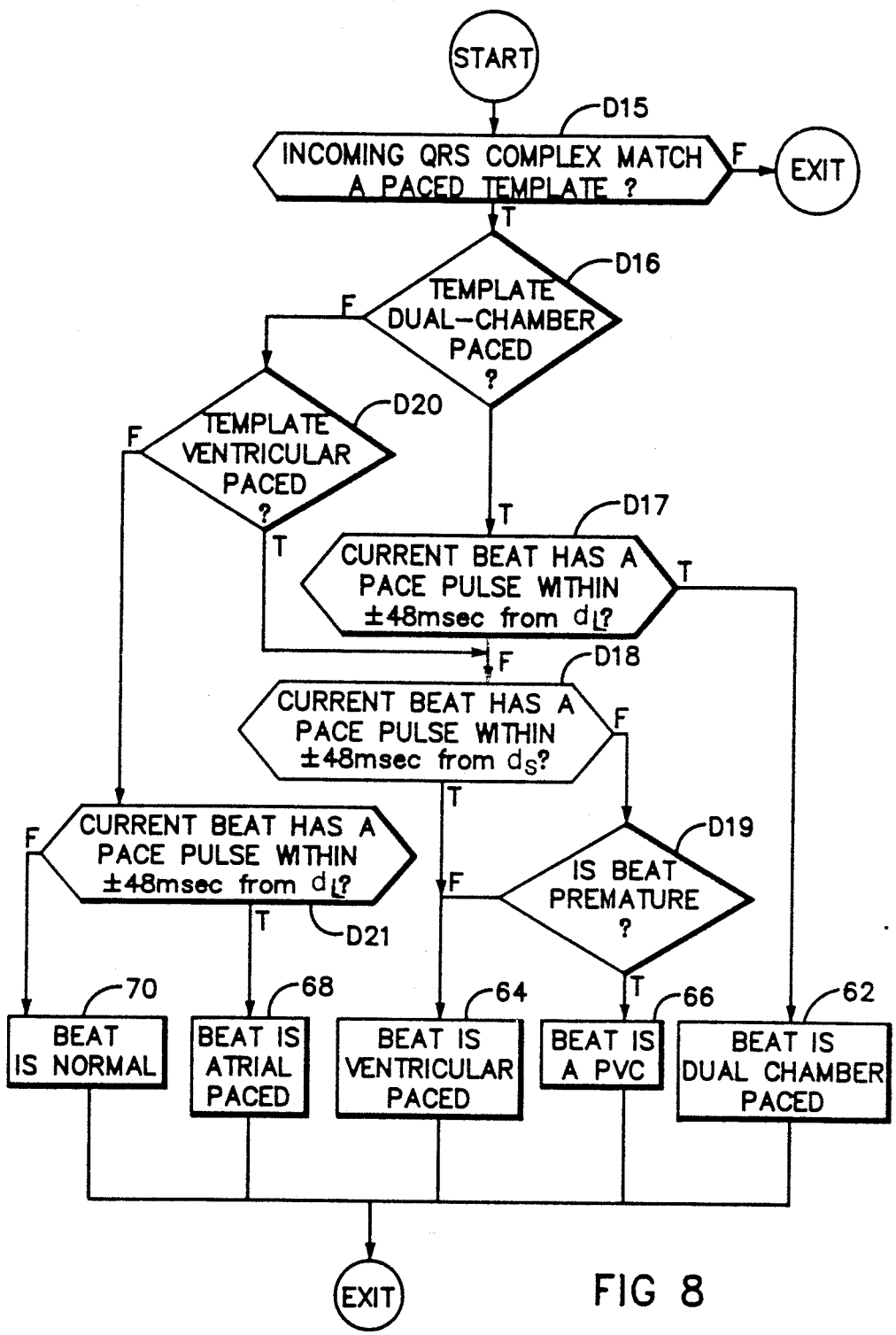
FIG. 8 is a flow chart for determining the classification of a current QRS complex.

The purpose of this procedure, FIG. 8, is to make a final classification of the current QRS complex. When this new complex arrived and was found by the QRS grouping means 10 to have a shape of one of the existing groups, the last eight complexes of that group with the current complex being the most recent one, are subjected to pace pulse clustering analysis 22, and paced templete classification 24.

D15 checks to see if the template classification is paced. If not, another classification is made, but if it is, D16 checks to see if the classification was dual-chamber paced. If so, D17 checks to see if the current QRS complex has a pace pulse within 48 msec of d1. If so the current QRS complex is classified as dual chamber paced by a block 62.

If D17 indicates that the current QRS complex does not have a pace pulse within 48 msec of d1, D18 checks to see if it has a pace pulse within 48 msec of ds. If so, a block 64 indicates that the current complex is ventricularly paced. If not, D19 checks to see if the QRS complex is premature i.e. early compared to paced beat intervals. If so, a block 66 classifies the complex as ectopic.

In the event that D16 indicates that the template classification is not dual chamber paced, D20 checks to see if the template classification was ventricularly paced. If it is the procedure goes to D18.

If D20 indicates that the template classification is not ventricularly paced, D21 checks to see if there is a pace pulse within 48 msec from d1. If so, block 68 classifies the complex as being atrially paced. If not, block 70 classifies the complex as normal.

If only one cluster is present, it can be detected by the procedure of FIG. 6A and the procedure of FIG. 6B so that the procedure shown in FIG. 7 for providing a group classification must take this into account. D9 of FIG. 7 will give a true signal and D10 will find that d1−ds is zero so that it will provide a true signal, but if two clusters have been detected that are separated by more than 120 msec, D10 will give a false signal and the block 54 will classify the group as being dual chamber paced. FIG. 7 would not have to perform this function if the procedures for detecting clusters took into account the expected different intervals for atrial pace pulses and ventricular pace pulses.

We claim:

1. An apparatus for classifying the type of pacing of QRS complexes in an ECG wave signal of a paced patient comprising, statistical means for detecting the times of occurrence of said QRS complexes in said ECG wave signal, means for detecting the times of occurrence of pace pulses in said ECG wave signal, means coupled to both of said means for determining the value of the time interval between each detected pace pulse and the next detected QRS complex to thereby provide at least one time interval value associated therewith, means for assigning said detected QRS complexes to respective groups in accordance with their shape, clustering means coupled to said last two means for detecting the existence of at least one cluster of time interval values occurring during a given number of most recent assigned QRS complexes of each group, means for deriving a representative interval value for each said cluster, and means for classifying a current QRS complex including means for comparing said at least one time interval value associated with it and the representative interval value or values for the at least one cluster of the group to which it has been assigned.

2. Apparatus as set forth in claim 1 wherein said classifying means classifies a current QRS complex as dual chamber paced when said clustering means has detected two clusters for the group to which the current QRS complex has been assigned that have respective representative interval values differing by at least a given amount of time and any interval value of the current QRS complex is within a different given amount of time of the longer representative interval value.

3. Apparatus as set forth in claim 1 wherein said classifying means classifies a current QRS complex as ventricularly paced when said clustering means has detected only one cluster for the group to which the current QRS complex has been assigned that has a representative interval value less than a given amount of time and any interval value of the current QRS complex is within a different given amount of time of the representative interval.

4. Apparatus as set forth in claim 1 wherein said classifying means classifies a current QRS complex as atrially paced when said clustering means has detected only one cluster for the group to which the current QRS complex has been assigned that has a representative interval value greater than a given amount of time and any interval value of the current QRS complex is within a different given amount of time of the representative interval value.

5. Apparatus as set forth in claim 1 wherein said classifying means classifies a current QRS complex as normal when said clustering means has detected only one cluster for the group to which the current QRS complex has been assigned that has a representative interval value greater than a given amount of time and any interval value of the current QRS complex differs from the representative interval value by at least a different given amount of time.

6. Apparatus as set forth in claim 1 wherein said classifying means classifies a current QRS complex as ectopic when said clustering means has detected two clusters for the group to which the current QRS complex has been assigned that have respective representative interval values differing by at least a given amount of time and any interval values of the current QRS complex differ from both representative interval values by at least a different given amount of time and the current QRS complex is premature in time.

7. Apparatus as set forth in claim 1 wherein said classifying means classifies a current QRS complex as ectopic when said clustering means has detected only one cluster for the group to which the current QRS complex has been assigned that has a representative interval value less than a given amount of time and any interval values of the current QRS complex differ from the representative interval value by at least a different given amount of time.

* * * * *